United States Patent
Wang et al.

(10) Patent No.: US 10,660,773 B2
(45) Date of Patent: May 26, 2020

(54) CRIMPING METHODS FOR THIN-WALLED SCAFFOLDS

(71) Applicant: Abbott Cardiovascular Systems Inc., Santa Clara, CA (US)

(72) Inventors: Karen J. Wang, Sunnyvale, CA (US); Edward P. Garcia, Dublin, CA (US); Boyd V. Knott, Menifee, CA (US); Jill A. McCoy, Sunnyvale, CA (US); Ashleigh Z. Sheehy, Santa Clara, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 226 days.

(21) Appl. No.: 15/432,837

(22) Filed: Feb. 14, 2017

(65) Prior Publication Data
US 2018/0228630 A1    Aug. 16, 2018

(51) Int. Cl.
*B29C 65/66*    (2006.01)
*A61F 2/958*    (2013.01)
(Continued)

(52) U.S. Cl.
CPC .............. *A61F 2/958* (2013.01); *B29C 65/66* (2013.01); *B29C 65/7817* (2013.01); *B29C 66/532* (2013.01); *B29C 66/63* (2013.01); *B29C 66/71* (2013.01); *B29C 66/73117* (2013.01); *B29C 66/73791* (2013.01); *B29C 67/0014* (2013.01); *A61F 2/04* (2013.01); *A61F 2/915* (2013.01);
(Continued)

(58) Field of Classification Search
CPC .... A61F 2/958; A61F 2/95; A61F 2002/9522; A61F 2250/0067; B29D 23/00; Y10T 29/4994; Y10T 29/49927; Y10T 29/49945; Y10T 29/49925; Y10T 29/53996; Y10T 29/49908
See application file for complete search history.

(56) References Cited

U.S. PATENT DOCUMENTS 5,261,263 A    11/1993    Whitesell
5,556,383 A    9/1996    Wang et al.
(Continued)

FOREIGN PATENT DOCUMENTS

CN    1260213    7/2000
CN    101015440    8/2007
(Continued)

OTHER PUBLICATIONS

U.S. Appl. No. 11/330,927, filed Jan. 11, 2006, Wu et al.
(Continued)

*Primary Examiner* — Sarang Afzali
*Assistant Examiner* — Ruth G Hidalgo-Hernandez
(74) *Attorney, Agent, or Firm* — Squire Patton Boggs (US) LLP

(57) ABSTRACT

A medical device includes a balloon expanded scaffold crimped to a catheter having a balloon. The scaffold has a network of rings formed by struts connected at crowns and links connecting adjacent rings. The scaffold is crimped to the balloon by a process that includes using protective polymer sheaths or sheets during crimping, and adjusting the sheaths or sheets during the crimping to avoid or minimize interference between the polymer material and scaffold struts as the scaffold is reduced in size.

20 Claims, 9 Drawing Sheets

(51) Int. Cl.
*B29C 65/00* (2006.01)
*B29C 67/00* (2017.01)
*B29C 65/78* (2006.01)
*A61F 2/95* (2013.01)
*A61F 2/915* (2013.01)
*A61F 2/04* (2013.01)
*B29L 28/00* (2006.01)
*B29L 31/00* (2006.01)
*B29C 65/82* (2006.01)

(52) U.S. Cl.
CPC .............. *A61F 2002/91566* (2013.01); *A61F 2002/9522* (2013.01); *B29C 65/8246* (2013.01); *B29C 66/91411* (2013.01); *B29C 66/91941* (2013.01); *B29C 66/91945* (2013.01); *B29C 66/929* (2013.01); *B29C 66/949* (2013.01); *B29C 2793/0009* (2013.01); *B29L 2028/00* (2013.01); *B29L 2031/7543* (2013.01)

(56) References Cited

U.S. PATENT DOCUMENTS

| | | |
|---|---|---|
| 5,672,169 A | 9/1997 | Verbeek |
| 5,836,965 A | 11/1998 | Jendersee et al. |
| 5,913,871 A | 6/1999 | Werneth et al. |
| 5,976,181 A | 11/1999 | Whelan et al. |
| 5,992,000 A | 11/1999 | Humphrey et al. |
| 6,018,857 A | 2/2000 | Duffy et al. |
| 6,063,092 A | 5/2000 | Shin |
| 6,092,526 A | 7/2000 | LaFontaine et al. |
| 6,179,867 B1 | 1/2001 | Cox |
| 6,305,436 B1 | 10/2001 | Andersen et al. |
| 6,312,459 B1 | 11/2001 | Huang et al. |
| 6,360,577 B2 | 3/2002 | Austin |
| 6,488,688 B2 | 12/2002 | Lim et al. |
| 6,629,350 B2 | 10/2003 | Motsenbocker |
| 6,666,880 B1 | 12/2003 | Chiu et al. |
| 6,745,445 B2 | 6/2004 | Spilka |
| 6,783,542 B2 | 8/2004 | Eidenschink |
| 6,805,703 B2 | 10/2004 | McMorrow |
| 6,863,683 B2 | 3/2005 | Schwager et al. |
| 6,931,899 B2 | 8/2005 | Goff et al. |
| 7,010,850 B2 | 3/2006 | Hijlkema et al. |
| 7,156,869 B1 | 1/2007 | Pacetti |
| 7,316,148 B2 | 1/2008 | Asmus et al. |
| 7,389,670 B1 | 6/2008 | Kokish et al. |
| 7,563,400 B2 | 7/2009 | Wilson et al. |
| 7,648,727 B2 | 1/2010 | Hossainy et al. |
| 7,761,968 B2 | 7/2010 | Huang et al. |
| 7,762,804 B1 | 7/2010 | Stupecky |
| 7,763,198 B2 | 7/2010 | Knott et al. |
| 7,886,419 B2 | 2/2011 | Huang et al. |
| 7,945,409 B2 | 5/2011 | Furst et al. |
| 7,947,207 B2 | 5/2011 | McNiven et al. |
| 7,951,185 B1 | 5/2011 | Abbate et al. |
| 7,971,333 B2 | 7/2011 | Gale et al. |
| 8,002,817 B2 | 8/2011 | Limon |
| 8,046,897 B2 | 11/2011 | Wang et al. |
| 8,123,793 B2 | 2/2012 | Roach et al. |
| 8,225,474 B2 | 7/2012 | Arcand et al. |
| 8,261,423 B2 | 9/2012 | Jow et al. |
| 8,323,760 B2 | 12/2012 | Zheng et al. |
| 8,425,587 B2 | 4/2013 | Trollsas et al. |
| 8,539,663 B2 | 9/2013 | Wang et al. |
| 8,568,471 B2 | 10/2013 | Troikas et al. |
| 8,595,913 B2 | 12/2013 | Knott et al. |
| 8,726,483 B2 | 5/2014 | Stankus et al. |
| 8,752,261 B2 | 6/2014 | Van Sciver |
| 8,752,265 B2 | 6/2014 | Wang |
| 8,844,113 B2 | 9/2014 | Wang |
| 8,961,848 B2 | 2/2015 | Roberts et al. |
| RE45,744 E | 10/2015 | Gale et al. |
| 9,155,870 B2 | 10/2015 | Wang |
| 9,199,408 B2 | 12/2015 | Wang et al. |
| 9,283,100 B2 | 3/2016 | Wang et al. |
| 9,308,106 B2 | 4/2016 | Knott et al. |
| 9,642,729 B2 | 5/2017 | Wang et al. |
| 9,681,971 B2 | 6/2017 | Wang |
| 9,724,219 B2 | 8/2017 | Wang |
| 9,895,241 B2 | 2/2018 | Wang |
| 9,931,787 B2 | 4/2018 | Harrington et al. |
| 9,999,527 B2 | 6/2018 | Pacetti et al. |
| 2002/0035774 A1 | 3/2002 | Austin |
| 2002/0143382 A1 | 10/2002 | Hijlkema et al. |
| 2003/0070469 A1 | 4/2003 | Kokish |
| 2004/0078953 A1 | 4/2004 | Spilka |
| 2004/0096538 A1 | 5/2004 | Goff et al. |
| 2004/0106973 A1 | 6/2004 | Johnson |
| 2004/0138731 A1 | 7/2004 | Johnson |
| 2004/0181236 A1 | 9/2004 | Eidenschink et al. |
| 2004/0260379 A1 | 12/2004 | Jagger et al. |
| 2005/0119720 A1 | 6/2005 | Gale et al. |
| 2005/0143752 A1 | 6/2005 | Schwager et al. |
| 2005/0159802 A1 | 7/2005 | Furst et al. |
| 2005/0183259 A1 | 8/2005 | Eidenschink et al. |
| 2005/0188525 A1 | 9/2005 | Weber et al. |
| 2005/0229670 A1 | 10/2005 | Perreault |
| 2005/0244533 A1 | 11/2005 | Motsenbocker et al. |
| 2005/0283225 A1 | 12/2005 | Klisch |
| 2006/0004469 A1 | 1/2006 | Sokel |
| 2006/0047336 A1 | 3/2006 | Gale et al. |
| 2006/0100694 A1 | 5/2006 | Globerman |
| 2006/0116748 A1 | 6/2006 | Kaplan et al. |
| 2006/0123874 A1 | 6/2006 | Motsenbocker |
| 2006/0196073 A1 | 9/2006 | Parker |
| 2007/0006441 A1 | 1/2007 | McNiven et al. |
| 2007/0023974 A1 | 2/2007 | Wu |
| 2007/0204455 A1 | 9/2007 | Knott et al. |
| 2007/0259099 A1 | 11/2007 | Van Sciver |
| 2007/0271763 A1 | 11/2007 | Huang et al. |
| 2007/0282433 A1 | 12/2007 | Limon et al. |
| 2007/0289117 A1 | 12/2007 | Huang et al. |
| 2007/0293938 A1 | 12/2007 | Gale et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0033526 A1 | 2/2008 | Atladottir et al. |
| 2008/0072653 A1 | 3/2008 | Gillick et al. |
| 2008/0127707 A1 | 6/2008 | Kokish et al. |
| 2008/0147164 A1 | 6/2008 | Gale et al. |
| 2008/0208327 A1 | 8/2008 | Rowe |
| 2008/0275537 A1 | 11/2008 | Limon |
| 2009/0001633 A1 | 1/2009 | Limon et al. |
| 2009/0088829 A1 | 4/2009 | Wang et al. |
| 2009/0105800 A1 | 4/2009 | Sabaria |
| 2009/0133817 A1 | 5/2009 | Sabaria |
| 2009/0228094 A1 | 9/2009 | Yan et al. |
| 2009/0282669 A1 | 11/2009 | Von Oepen et al. |
| 2009/0287289 A1 | 11/2009 | Sagedahl et al. |
| 2009/0299452 A1 | 12/2009 | Eidenschink et al. |
| 2010/0004735 A1 | 1/2010 | Yang et al. |
| 2010/0025894 A1 | 2/2010 | Kleiner et al. |
| 2010/0063571 A1 | 3/2010 | Roach et al. |
| 2010/0087782 A1 | 4/2010 | Ghaffari et al. |
| 2010/0115755 A1 | 5/2010 | Pacetti |
| 2010/0286758 A1 | 11/2010 | Berglund |
| 2010/0323091 A1 | 12/2010 | Castro et al. |
| 2011/0152905 A1 | 6/2011 | Eaton |
| 2011/0190872 A1 | 8/2011 | Anukhin et al. |
| 2011/0270383 A1 | 11/2011 | Jow et al. |
| 2011/0271513 A1 | 11/2011 | Wang |
| 2011/0307046 A1 | 12/2011 | Bourang et al. |
| 2012/0010693 A1 | 1/2012 | Van Sciver |
| 2012/0017416 A1 | 1/2012 | Wang et al. |
| 2012/0042501 A1 | 2/2012 | Wang et al. |
| 2012/0079706 A1 | 4/2012 | Knott et al. |
| 2012/0285609 A1 | 11/2012 | Wang |
| 2012/0316635 A1 | 12/2012 | Jow et al. |
| 2013/0255853 A1 | 10/2013 | Wang et al. |
| 2014/0013575 A1 | 1/2014 | Wang et al. |
| 2014/0033506 A1 | 2/2014 | Jow et al. |
| 2014/0096357 A1 | 4/2014 | Wang |

(56) References Cited

U.S. PATENT DOCUMENTS

| | | | |
|---|---|---|---|
| 2014/0189994 A1 | 7/2014 | Van Sciver | |
| 2014/0230225 A1 | 8/2014 | Van Sciver | |
| 2014/0330363 A1* | 11/2014 | Anukhin | A61F 2/82 623/1.16 |
| 2014/0336747 A1 | 11/2014 | Rapoza et al. | |
| 2015/0059960 A1 | 3/2015 | Roberts et al. | |
| 2015/0257907 A1 | 9/2015 | Vial et al. | |
| 2016/0081824 A1 | 3/2016 | Harrington et al. | |
| 2017/0172768 A1 | 6/2017 | Ta et al. | |
| 2017/0348124 A1 | 12/2017 | Wang | |
| 2018/0116830 A1 | 5/2018 | Wang | |
| 2019/0133798 A1 | 5/2019 | Gong et al. | |
| 2019/0375146 A1 | 12/2019 | Wang et al. | |

FOREIGN PATENT DOCUMENTS

| | | |
|---|---|---|
| EP | 0 787 020 | 8/1997 |
| EP | 1 000 591 | 5/2000 |
| EP | 1 226 798 | 7/2002 |
| EP | 1 295 570 | 3/2003 |
| EP | 1 818 073 | 8/2007 |
| EP | 2 029 052 | 3/2009 |
| JP | 2005-535459 | 11/2005 |
| JP | 2008-538940 | 11/2008 |
| JP | 2009-540928 | 11/2009 |
| JP | 2009-542263 | 12/2009 |
| JP | 4468333 | 5/2010 |
| JP | 2010-525903 | 7/2010 |
| JP | 2010-540091 | 12/2010 |
| WO | WO 99/55406 | 11/1999 |
| WO | WO 00/36994 | 6/2000 |
| WO | WO 01/35861 | 5/2001 |
| WO | WO 02/074192 | 9/2002 |
| WO | WO 02/102283 | 12/2002 |
| WO | WO 2004/016369 | 2/2004 |
| WO | WO 2005/053937 | 6/2005 |
| WO | WO 2006/110861 | 10/2006 |
| WO | WO 2006/117016 | 11/2006 |
| WO | WO 2007/116305 | 10/2007 |
| WO | WO 2007/146354 | 12/2007 |
| WO | WO 2007/146543 | 12/2007 |
| WO | WO 2007/149464 | 12/2007 |
| WO | WO 2008/011028 | 1/2008 |
| WO | WO 2008/033621 | 3/2008 |
| WO | WO 2008/137821 | 11/2008 |
| WO | WO 2009/045764 | 4/2009 |
| WO | WO 2010/036982 | 4/2010 |
| WO | WO 2010/151497 | 12/2010 |
| WO | WO 2011/136929 | 11/2011 |
| WO | WO 2012/006451 | 1/2012 |
| WO | WO 2012/027172 | 3/2012 |
| WO | WO 2012/044454 | 4/2012 |
| WO | WO 2012/145326 | 10/2012 |
| WO | WO 2013/039637 | 3/2013 |

OTHER PUBLICATIONS

U.S. Appl. No. 11/938,127, filed Nov. 9, 2007, Wang.
Angioplasty Summit Abstracts/Oral, Am J Cardiol. Apr. 23-26, 2013, p. 23B.
Bosiers et al., "Coronary and endovascular applications of the Absorb™ bioresorbable vascular scaffold", Interv Cardiol. 2012; 4(6): 621-631.
Miller, R., "Abbott's Bioresorbable Stent Shows Durable Results in ABSORB Trial", The Gray Sheet, Mar. 25, 2013, pp. 17-18.
Zhang et al., "Heparin-and basic fibroblast growth factor-incorporated degradable stent: comparison with traditional transmyocardial revascularization", J Cardiovasc Surg. 2011; 52: 261-270.
International Preliminary Report on Patentability dated Aug. 29, 2019, in International Patent Application No. PCT/US2018/017869, 7 pages.

* cited by examiner

CRIMPING METHODS FOR THIN-WALLED SCAFFOLDS

BACKGROUND OF THE INVENTION

Field of the Invention

The present invention relates to medical devices; more particularly, this invention relates to processes for uniformly crimping and deploying a medical device, such as a polymeric scaffold, to and from, respectively, a delivery balloon.

Description of the State of the Art

Radially expandable endoprostheses are artificial devices adapted to be implanted in an anatomical lumen. An "anatomical lumen" refers to a cavity, or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. Scaffolds may also be constructed of bioerodible metals and alloys. The scaffold, as opposed to a durable metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorbable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(D,L-lactide-co-glycolide) ("PLGA"), poly(D-lactide-co-glycolide) or poly(L-lactide-co-D-lactide) ("PLLA-co-PDLA") with less than 10% D-lactide, poly(L-lactide-co-caprolactone), poly(caprolactone), PLLA/PDLA stereo complex, and blends of the aforementioned polymers may be described, through comparison with a metallic material used to form a stent, in some of the following ways. Polymeric materials typically possess a lower strength to volume ratio compared to metals, which means more material is needed to provide an equivalent mechanical property. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymers such as PLLA or PLGA.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris or sliding-wedge types, or other types of crimping mechanisms. A significant amount of plastic or inelastic deformation occurs both when the balloon expandable stent or scaffold is crimped and later deployed by a balloon. At the treatment site within the lumen, the stent is expanded by inflating the balloon. The expanded state is achieved and maintained, substantially, if not entirely by an irreversible or inelastic strain at the crowns of the stent or scaffold caused by the balloon expansion. Self-expanding stents or scaffolds, by contrast, achieve and maintain their expanded state in the vessel by an elastic, radially outward force.

A film-headed crimper has been used to crimp stents to balloons. Referring to FIG. 1A, there is shown a perspective view of a crimping assembly 20 that includes three rolls 123, 124, 125 used to position a clean sheet of non-stick material between the crimping blades and the stent prior to crimping. For example, upper roll 125 holds the sheet secured to a backing sheet. The sheet is drawn from the backing sheet by a rotating mechanism (not shown) within the crimper head 21. A second sheet is dispensed from the mid roll 124. After crimping, the first and second (used) sheets are collected by the lower roll 123. As an alternative to rollers dispensing a non-stick sheet, a stent may be covered in a thin, compliant protective sheath before crimping.

FIG. 1B illustrates the positioning the first sheet 125a and second sheet 124a relative to the wedges 22 and a stent 100 within the aperture of the crimping assembly 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material (or protective sheath) are used to avoid buildup of coating material on the crimper blades for stents coated with a therapeutic agent. The sheets 125a, 124a are replaced by a new sheet after each crimping sequence. By advancing a clean sheet after each crimp, accumulation of contaminating coating material from previously crimped stents is avoided. By using replaceable sheets, stents having different drug coatings can be crimped using the same crimping assembly without risk of contamination or buildup of coating material from prior stent crimping.

There is a continuing need to improve upon methods for crimping a medical device and, in particular, a polymer scaffold to a delivery balloon in order to improve upon the uniformity of deployment of a polymer scaffold from the balloon, to increase the retention force between scaffold and balloon, and to obtain a minimal crossing profile for delivery of the scaffold to a target site.

SUMMARY OF THE INVENTION

The invention provides methods for crimping a balloon-expanded scaffold to a balloon catheter. According to one embodiment the inventive methods disclosed herein are used to improve upon a crimping process for a thin-walled scaffold. The process may alternatively be used to improve-upon a crimp process used to crimp scaffolds that have thicker walls.

Referring to the case of a thin-walled scaffold, it has been realized through testing a need to modify aspects of a crimping process that did not pose significant problems when a higher wall thickness scaffold was crimped using the same process. An example of a scaffold having a higher wall thickness is described in US 2010/0004735. It has been found that when a significant reduction in wall thickness is made (e.g., from 158 microns or about 160 microns wall thickness down to 100 microns wall thickness or less) prior methods of crimping have proven unsatisfactory. Those prior methods of crimping produced high numbers of twisted, cracked or fractured struts when applied to thin-walled scaffolds.

According to the invention, it has been determined that modifications to a crimping process may better ensure that all four of the following objectives are met:

Structural integrity: avoiding damage to the scaffold's structural integrity when the scaffold is crimped to the balloon, or expanded by the balloon.

Safe delivery to an implant site: avoiding dislodgement or separation of the scaffold from the balloon during transit to an implant site and having a small crossing profile for the catheter.

Uniformity of expansion: avoiding non-uniform expansion of scaffold rings, which can lead to structural failure and/or reduced fatigue life.

Avoidance of balloon over-stretch: monitoring of balloon pressure in relation to decreasing scaffold size to avoid excessive strain or possible pin-hole leaks in the balloon and without compromising the three prior needs.

According to the embodiments, a polymer scaffold is crimped to a balloon of a balloon catheter using a crimping device and polymer material disposed between the surfaces of the scaffold and faces of crimper blades that bear down on the scaffold during crimping. In a preferred embodiment the polymer material are sheets provided with a film-headed crimping device. According to this embodiment, the scaffold is crimped down in intermittent fashion. Between one or more crimping stages the polymer sheets are adjusted to remove slack or excess accumulated sheet material. After this re-setting of the polymer sheets the scaffold diameter is reduced down further, which may be followed subsequently by another re-setting of the polymer sheets, as necessary or desired. The number of re-sets of the polymer sheets will in general depend on the degree of diameter reduction during crimping, and more specifically will depend upon the crimping results, type of scaffold being crimped and material of the scaffold.

In an alternative, but less preferred embodiment the polymer material are sheaths placed over the scaffold. According to this embodiment a sheath having a first size is placed over the scaffold. The scaffold diameter is then reduced down by a crimping device. After the scaffold is partially reduced in diameter, the first sheath is replaced by a second, smaller sheath, matching the reduced diameter of the scaffold. The first sheath is replaced by the second, smaller sheath to avoid interference with the crimping process. Although using sheaths is a possible alternative way of protecting the scaffold and avoiding interference with the movement of struts as they fold around crowns during crimping, it is believed a very cumbersome and time/labor intensive manner of protecting a scaffold.

The crimping process may be used for a polymer scaffold or metal stent. In either case the benefits of having polymer material removed to minimize interference with the crimping process may be necessary in order to avoid irregular crimping or damage to coating material.

According to the various aspects of the invention, there is a medical device, method for crimping, or method for assembly of a medical device comprising such a medical device having one or more, or any combination of the following things (1) through (17):

(1) The medical device is a stent or scaffold crimped to a balloon catheter.
(2) A crimping method applied using a polymer material disclosed within a crimp aperture and between crimper blades and a scaffold.
(3) Re-setting of a polymer material within an aperture of a crimper head.
(4) A sliding wedge or iris-type crimper is used including but not limited to a film-headed crimper.
(5) The scaffold has a before crimp diameter that is higher than a nominal diameter for the balloon of the balloon catheter to which the scaffold is crimped.
(6) There is at least 2, between 2 and 5 re-sets of polymer material during a crimp process.
(7) There is a dwell period of between 1 and 25 seconds for a stage of a crimping process prior to a final dwell.

(8) A process for crimping a thin-walled scaffold having a wall thickness of less than 125 microns, or less than 100 microns, or between 80 and 125 microns to a balloon.
(9) A scaffold having a pattern according to FIG. 5.
(10) Balloon pressurization during crimping may be nominal balloon pressure, and balloon pressure decreased (or relieved) after 50%-75% of the final crimp dwell period is complete.
(11) Balloon pressure relieved after about 50% to 60% reduction from the before crimping diameter.
(12) A re-setting of the polymer material takes place according to any combination of the following:
 (a) First re-set takes place after about 30-35% reduction from the before crimp diameter, depending on scaffold initial diameter size (smaller starting size means re-set more likely needed in this range). This re-set may correspond to the time when the scaffold is removed from the crimper and alignment checked (or switching to Balloon A);
 (b) Two or more re-sets may be chosen based on the total travel from initial diameter to final crimp diameter; e.g., for diameter reductions of 2:1 (initial diameter to final diameter) use 2 re-sets, for 3:1 or above 3:1 use 3 or more re-sets;
 (c) For scaffold designs where struts closer together use more resets;
 (d) Employ a re-set whenever there has been a diameter reduction of about 30-35% between stages, but not to exceed in total 2, 3 or 4 re-sets for the entire crimping process; and/or
 (e) Limit to maximum of 5 or between 2 and 5 re-sets. However, more re-sets are certainly possible and may be needed to achieve a desired outcome.
(13) A method, comprising: using a scaffold made from a tube comprising a polymer, the polymer having a glass transition temperature, the scaffold having an outer diameter and the outer diameter having a before crimping size; using a balloon having a nominal diameter; using a crimping device having a plurality of blades configured to form an aperture, wherein the blades are rotated relative to each other to increase or decrease the size of the aperture during crimping; using a polymer material disposed within the aperture; and crimping the scaffold to the balloon, the crimping comprising: placing the scaffold and balloon within the aperture, wherein the polymer material is between a surface of the scaffold and a surface of the blades, reducing the diameter of the scaffold from the before crimping size to a first size, while the scaffold has about the first size, resetting the polymer material within the aperture, reducing the diameter of the scaffold from the first size to a second size, while the scaffold has about the second size, resetting the polymer material within the aperture.
(14) The method of (13), (15) or (16) in combination with one or more, or any of items (a)-(l):
 (a) wherein the crimping device is a film-headed crimper.
 (b) wherein the polymer material are polymer sheets.
 (c) wherein the polymer material comprises a plurality of sheaths.
 (d) wherein the scaffold has a crimping temperature during crimping.
 (e) wherein the before crimping size is greater than the nominal diameter of the balloon.
 (f) wherein the balloon is pressurized during each of the reducing the diameter steps.
 (g) the crimping step further including the step of removing the scaffold and balloon from the crimping device after the scaffold diameter is reduced to the first diameter, then returning the scaffold to the crimping device.
 (h) wherein the re-setting of the polymer material while the scaffold has about the first size occurs when the scaffold and balloon are removed from the crimping device.
 (i) wherein the balloon is a first balloon, further including the step of replacing the first balloon with a second balloon of a balloon catheter when the scaffold is removed from the crimping device, and the scaffold is crimped to the second balloon.
 (j) wherein the scaffold diameter is reduced from the before crimping diameter to the first diameter using a first crimping device, and the scaffold diameter is reduced from the first size to the second size using a second crimping device.
 (k) wherein the polymer material within the aperture is re-set more than 2 times during the crimping.
 (l) wherein before and after reducing the scaffold diameter from the first size to the second size the aperture is held constant while the balloon has the nominal diameter.
(15) A method, comprising: using a scaffold made from a tube comprising a polymer, the polymer having a glass transition temperature, the scaffold having an outer diameter and the outer diameter having a before crimping size; using a balloon having a nominal diameter; using a polymer material disposable within the aperture; and using a crimping device having a plurality of blades configured to form an aperture, wherein the blades are rotated relative to each other to increase or decrease a size of the aperture during crimping; and crimping the scaffold to the balloon, the crimping comprising: placing the scaffold and balloon within the aperture, reducing the diameter of the scaffold from the before crimping size to a first size that is between 30% to 35% less than the before crimping size, after reducing the diameter to the first size, increasing the aperture size to remove a pressure of the blades from a surface of the scaffold, followed by removing excess polymer material from the aperture, and after removing the polymer material, decreasing the aperture size, reducing the scaffold diameter from the first size to a second size, and after reducing the diameter to the second size, increasing the aperture size to remove a pressure of the blades from a surface of the scaffold, followed by removing excess polymer material from the aperture.
(16) A method, comprising: using a scaffold made from a tube comprising a polymer, the polymer having a glass transition temperature, the scaffold having an outer diameter and the outer diameter having a before crimping size; using a balloon having a nominal diameter; using a crimping device having a plurality of blades configured to form an aperture; using a polymer material disposable within the aperture; and crimping the scaffold to the balloon, the crimping comprising: placing the scaffold and balloon within the aperture so that the polymer material is between a scaffold surface and a surface of the blades, reducing the diameter of the scaffold from the before crimping size to a second size, wherein the polymer material within the aperture is reset between 2 and 5 times while the scaffold diameter is reduced from the before crimping size to the second size.

(17) The method of (13), (15) or (16) in combination with one or more, or any of items (a)-(c):
(a) wherein the polymer material comprises sheaths having different sizes.
(b) wherein the polymer material are sheets operated by a film-headed crimper.
(c) wherein the scaffold comprises struts forming rings, wherein neighboring rings are connected to each other by at least two links, and the scaffold is crimped to a theoretical minimum crimp size (D-min).

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Figure 1A:
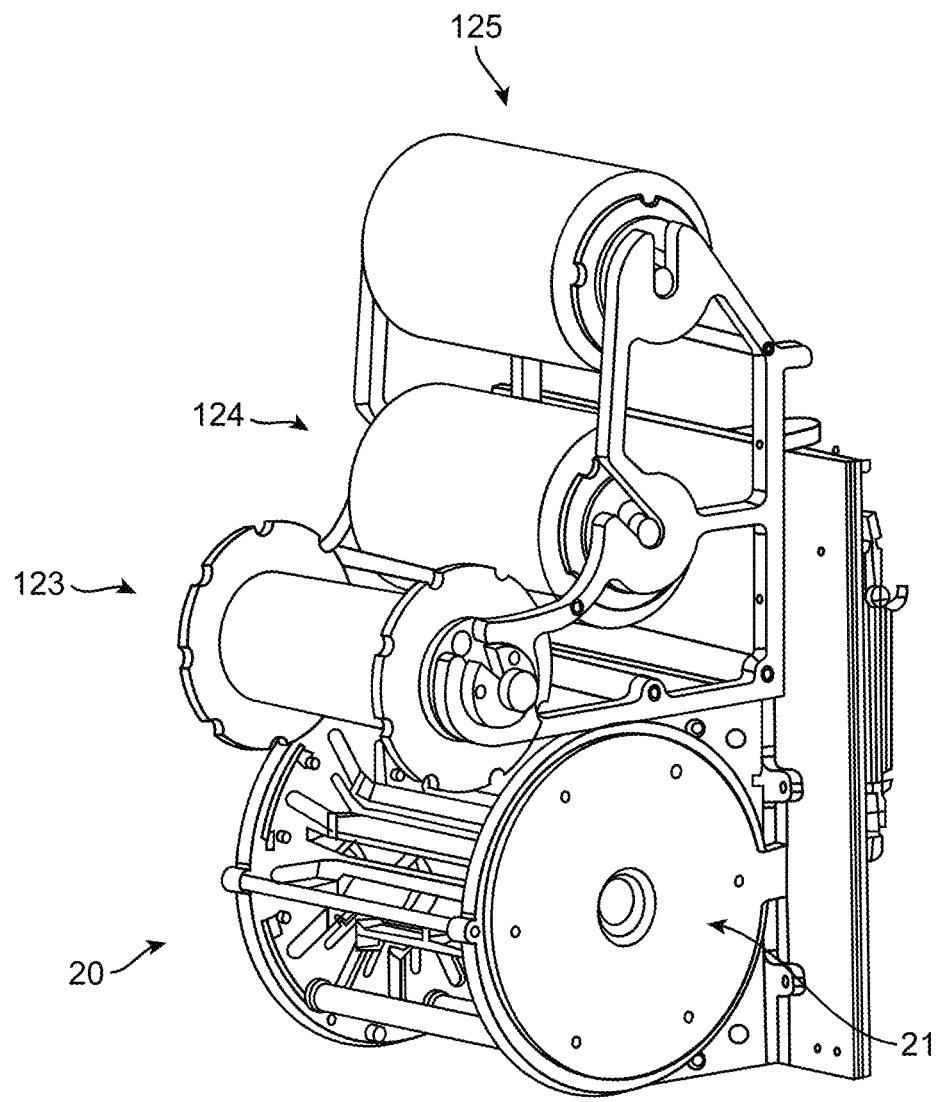
FIG. 1A is a perspective view of a prior art film-headed crimper.

In the description like reference numbers appearing in the drawings and description designate corresponding or like elements among the different views.

Definitions

For purposes of this disclosure, the following terms and definitions apply:

The terms "about," "approximately," "generally," or "substantially" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance or standard deviation from d1.

It is understood that any numerical value, range, or either range endpoint (including, e.g., "approximately none", "about none", "about all", etc.) preceded by the word "about," "approximately," "generally," or "substantially" in this disclosure also describes or discloses the same numerical value, range, or either range endpoint not preceded by the word "about," "approximately," "generally," or "substantially."

The "glass transition temperature," TG, is the temperature at which the amorphous domains of a polymer change from a brittle vitreous state to a solid deformable or ductile state at atmospheric pressure. This application defines TG and methods to find TG, or TG-low (the lower end of a TG range) for a polymer in the same way as in U.S. application Ser. No. 14/857,635.

A "stent" means a permanent, durable or non-degrading structure, usually comprised of a non-degrading metal or metal alloy structure, generally speaking, while a "scaffold" means a temporary structure comprising a bioresorbable or biodegradable polymer, metal, alloy or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the inner diameter or the outer diameter the scaffold attains when its supporting balloon is inflated to expand the scaffold from its crimped configuration to implant the scaffold within a vessel. The inflated diameter may refer to a post-dilation balloon diameter which is beyond the nominal diameter, or nominal inflated diameter for the balloon (e.g., a 6.5 mm balloon has a nominal diameter of 6.5 mm or when inflated to its nominal inflated diameter has a diameter of 6.5 mm). The scaffold diameter, after attaining its inflated or expanded diameter by balloon pressure, will to some degree decrease in diameter due to recoil effects related primarily to, any or all of, the manner in which the scaffold was fabricated and processed, the scaffold material and the scaffold design. When reference is made to a fully inflated diameter of a balloon, it refers to balloon pressurization corresponding to the nominal inflated diameter or greater than the nominal inflated diameter.

When reference is made to a diameter it shall mean the inner diameter or the outer diameter, unless stated or implied otherwise given the context of the description.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

Figure 1B:
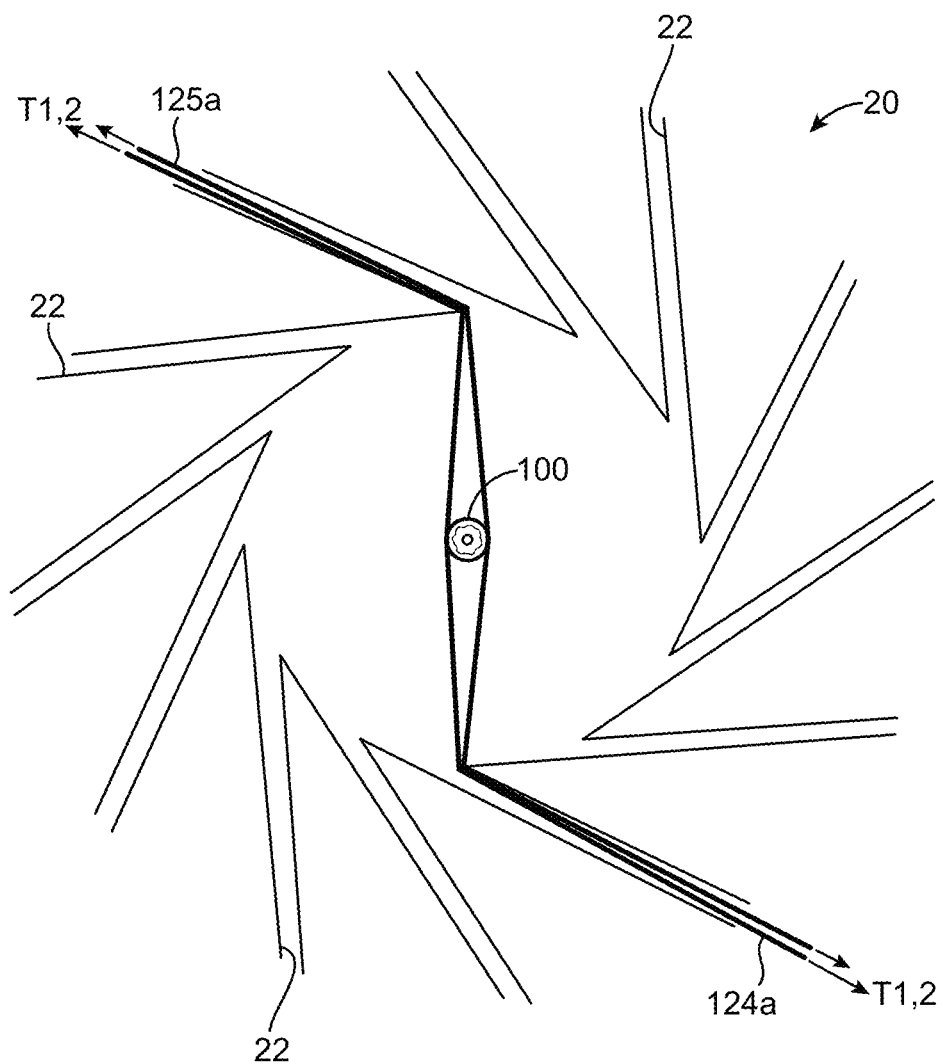
FIG. 1B is a frontal view of the head of the film-headed crimper of FIG. 1A as crimper jaws are being brought down on a stent.

A "before-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "before-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

A "crimping stage" or "stage" of a crimping process refers to a period of time when the jaws of a crimping device are held fixed, or the aperture of the crimp head is held at a constant diameter. The duration of the stage may be called a dwell period. Dwell periods can range from 1 sec to 25 sec, for initial stages prior to a final dwell. After the final crimped diameter is reached the dwell may be between 50 sec and 300 sec. The aperture of a crimping device is reduced from a first diameter to a second diameter when the crimping device moves from a first stage to a second stage, respectively. The aperture reduction sizes—e.g., from a first diameter or aperture size to second diameter or aperture size— are, for purposes of this disclosure, understood as being the same as the actual outer diameter of the scaffold within the aperture when the scaffold is being reduced in size by the crimper crimp. It is understood, however, that a programmed aperture size may not be exactly the same as the outer diameter of the crimped scaffold size, especially when a scaffold is being crimped to very small diameters.

A material "comprising" or "comprises" poly(L-lactide) or PLLA includes, but is not limited to, a PLLA polymer, a blend or mixture including PLLA and another polymer, and a copolymer of PLLA and another polymer. Thus, a strut comprising PLLA means the strut may be made from a material including any of a PLLA polymer, a blend or mixture including PLLA and another polymer, and a copolymer of PLLA and another polymer.

Figure 5:
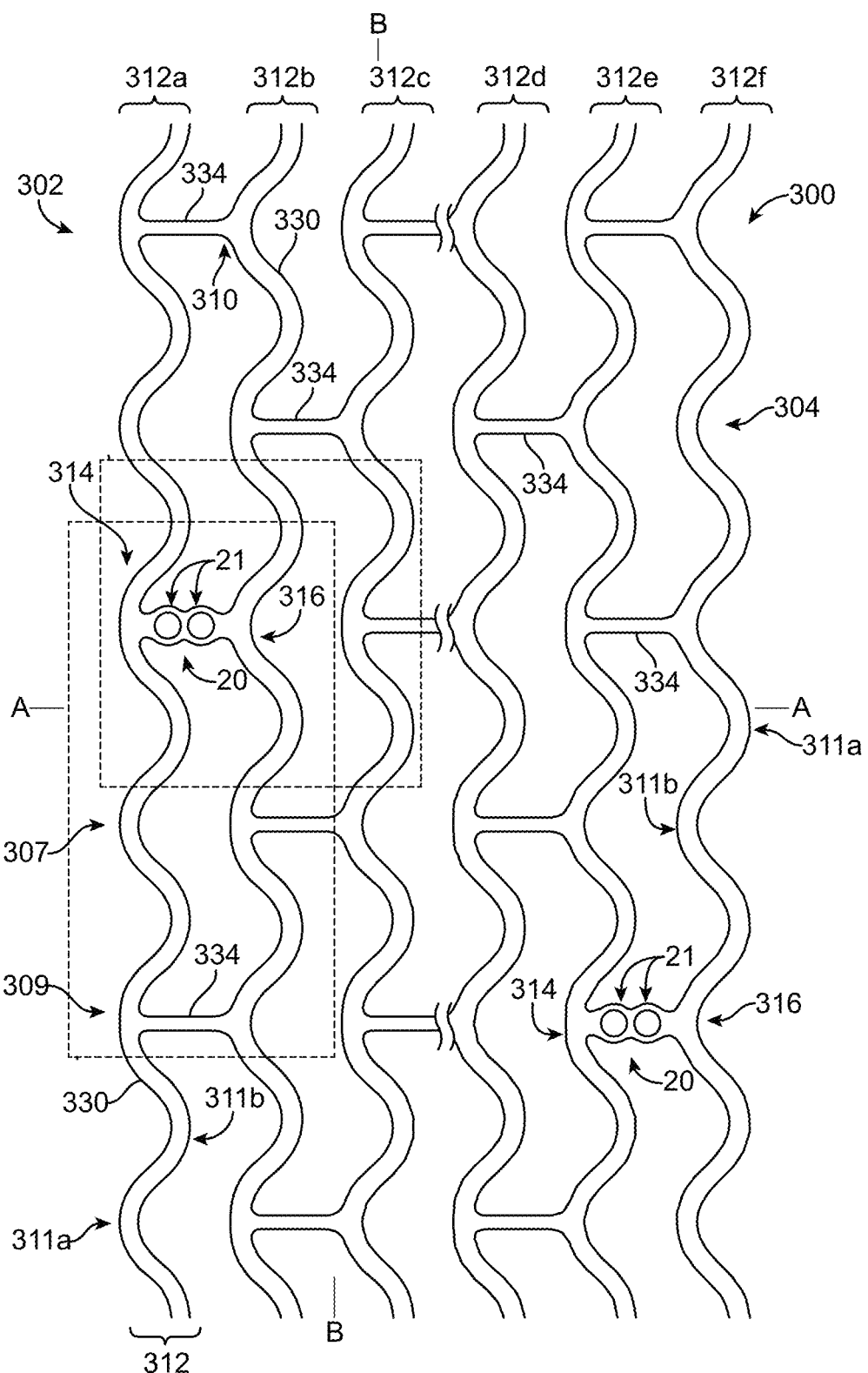
FIG. 5 shows distal and proximal end portions of a scaffold according to one embodiment.

When reference is made to a direction perpendicular to, or parallel with/to axis A-A (e.g., as shown in FIG. 5) it will mean perpendicular to, or parallel with/to the axial direction of a scaffold or tube. Similarly, When reference is made to a direction perpendicular to, or parallel with/to axis B-B (e.g., as shown in FIG. 5) it will mean perpendicular to, or parallel with/to the circumferential direction of the scaffold or tube. Thus, a sinusoidal ring of a scaffold extends parallel with/to (in periodic fashion) the circumferential direction or parallel to axis B-B, and perpendicular to axis A-A whereas a link in one embodiment extends parallel to the axial direction or axis A-A of the scaffold or tube and perpendicular to the axis B-B.

Wherever the same element numbering is used for more than one drawing it is understood the same description first used for the element in a first drawing applies to embodiments described in later drawings, unless noted otherwise.

The dimension of thickness (e.g., wall, strut, ring or link thickness) refers to a dimension measured perpendicular to both of axes A-A and B-B. The dimension of width is measured in the plane of axes A-A and B-B; more specifically, the width is the cross-sectional width from one side to another side of a contiguous structure; thus, link 334 has a constant link width. Moreover, it is understood that the so-called plane of axes A-A and B-B is technically not a plane since it describes surfaces of a tubular structure having central lumen axis parallel with axis A-A. Axis B-B therefore may alternatively be thought of as the angular component if the scaffold locations were being described using a cylindrical coordinate system (i.e., axis A-A is Z axis and location of a luminal/abluminal surface of a crown, link, ring, etc. is found by the angular coordinate and radial coordinate constant).

A "thin wall thickness," "thin-walled scaffold," "thin-wall" refers to a strut, ring, link, or bar arm made from a polymer comprising poly(L-lactide) and having a wall thickness less than 125 microns.

A "crimping temperature" according to the disclosure means a temperature above ambient and slightly less than, or about equal to the glass transition temperature (TG) for a polymer of the scaffold, e.g., poly(L-lactide). In a preferred embodiment the crimping temperature is between TG and 15 degrees less than TG, or between TG and 10 degrees, or 5 degrees less than TG. In other embodiments the crimping temperature is achieved by heating the scaffold to a temperature at least 20 degrees below TG and preferably to a temperature at least 15 degrees below TG.

Figure 3A:
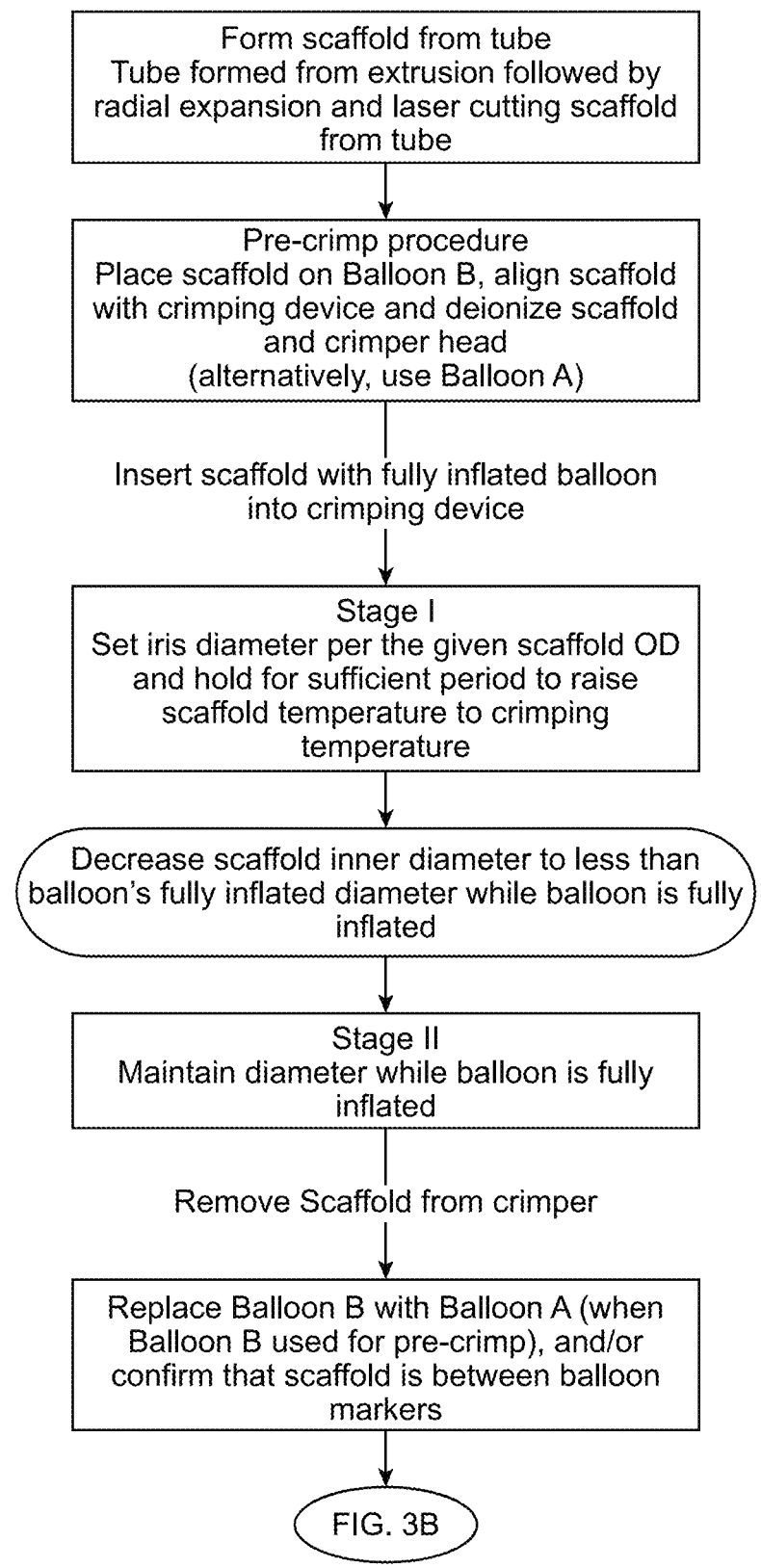
FIGS. 3A and 3B describe a first process (Process I) for crimping a scaffold according to the disclosure.
Figure 3B:
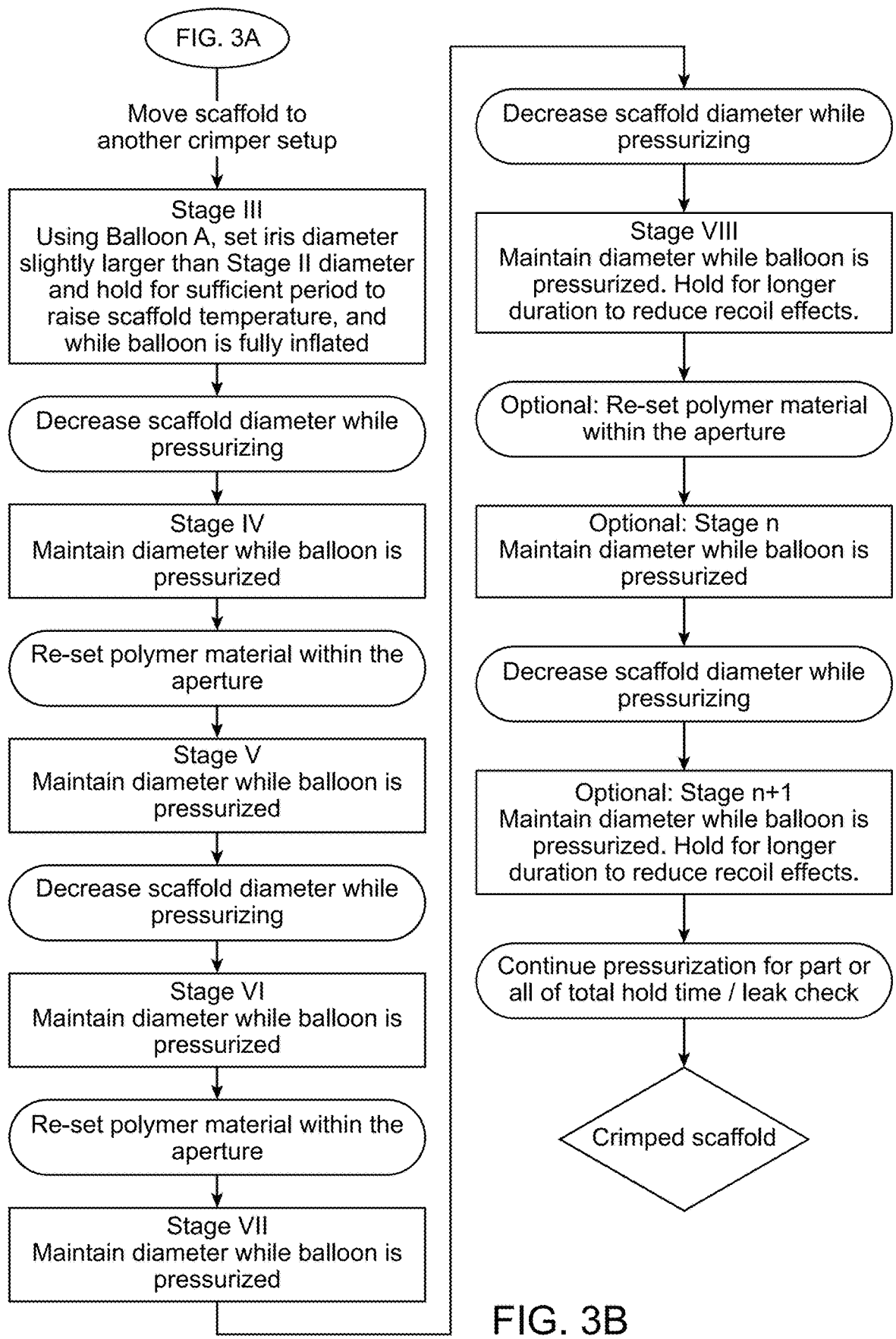
Figure 4A:
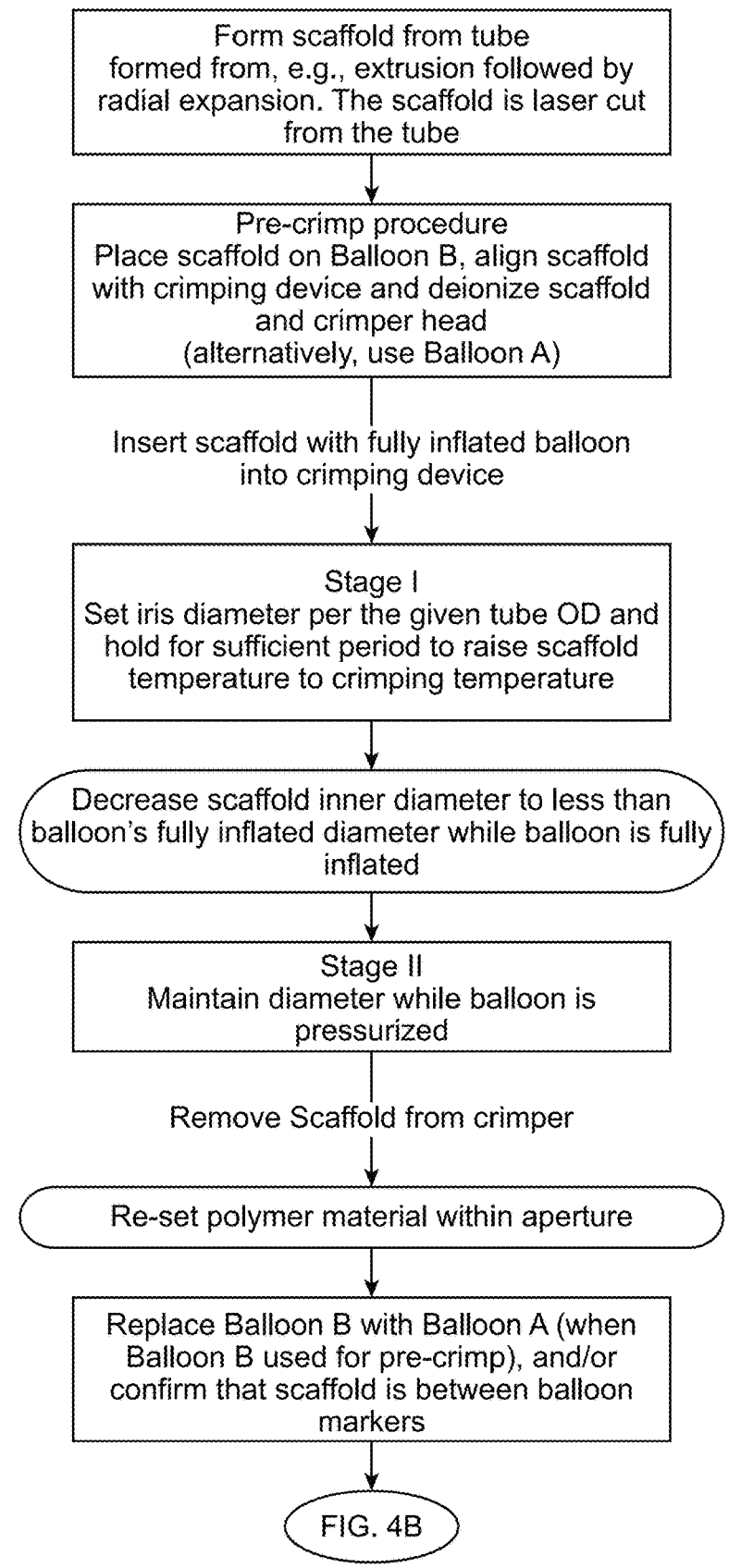
FIGS. 4A and 4B describe a second process (Process II) for crimping a scaffold according to the disclosure.
Figure 4B:
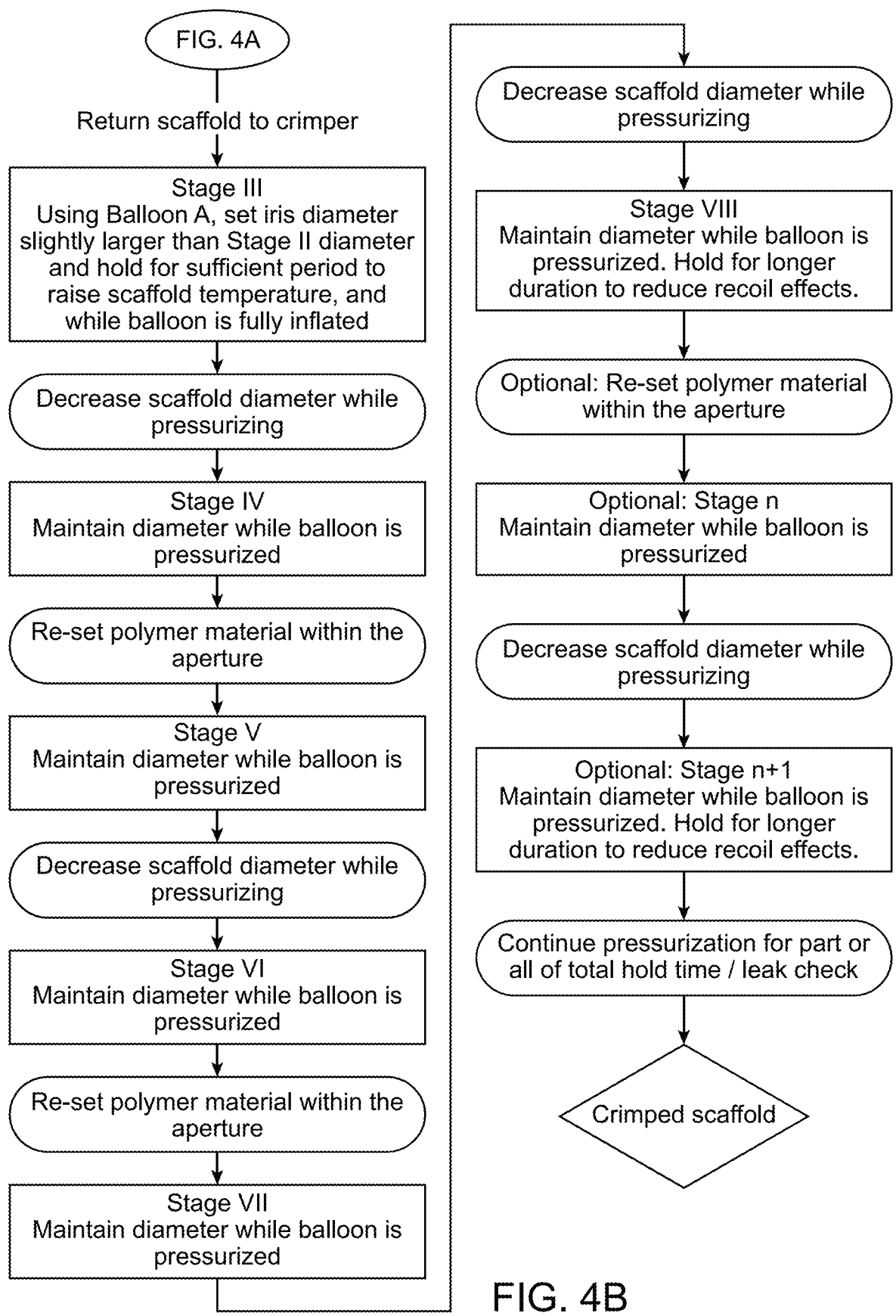

"Re-set of the polymer material within the aperture" as indicated in the crimping steps in FIGS. 3B and 4B or "resetting of the polymer material within the aperture", means one or both of removing excessive polymer material from within an aperture of a crimp head formed by the interconnected blades or wedges of a mechanical crimping device (e.g., an iris or sliding wedge type crimper) or increasing/opening the aperture sufficiently to remove blade pressure on the scaffold (in the case of a film-headed crimper). The blades or wedges converge upon the scaffold in order to reduce the diameter of the scaffold (and crimp the scaffold to the balloon). As example of a film-headed crimper is the MSI™ SC775S/875S, available from the Machine Solutions company. For this crimper re-set of the polymer material within the aperture is accomplished by fully opening the crimp aperture to cause the polymer sheet material to automatically return to its starting position and become fully taut and a fresh sheet of polymer material to spool. After this step, the aperture is then brought back down upon the scaffold to continue the crimping process.

Embodiments

An effective crimping process for a scaffold must at least satisfy each of the following objectives:

Structural integrity: avoiding damage to the scaffold's structural integrity when the scaffold is crimped to the balloon, or expanded by the balloon.

Safe delivery to an implant site: avoiding dislodgement or separation of the scaffold from the balloon during transit to an implant site.

Uniformity of expansion: avoiding non-uniform expansion of scaffold rings, which can lead to structural failure and/or reduced fatigue life.

As previously reported in US20140096357 a scaffold is not as resilient as a stent made from metal, which is highly ductile. Satisfying all of the above needs is therefore more challenging for a polymer scaffold, especially a thin-walled scaffold that can fracture more easily during crimping or balloon expansion and is more susceptible to twisting, flipping or overlap during crimping.

According to the disclosure there is a crimping process that includes steps where polymer material is re-set or replaced in the crimp head in order to minimize any interference between the compressing-down of the scaffold struts by crimper blades and the polymer material. The polymer material is used to protect the surface or the scaffold, or coating disposed over a scaffold (or stent). However, as the scaffold is crimped further down and its diameter decreases, the polymer material surrounding the scaffold when it had the larger diameter becomes excessive, resulting in folds, roll-up, slackening or loss of tension. Although a crimping mechanism may include a tensioning portion that applies a tensioning force as the aperture decreases (as a means to take-up excess slack in the polymer material) due to the presence of the blades in close proximity, or in contact with surfaces of the scaffold struts the tensioning force cannot remove material from near the scaffold. To address this problem a crimp aperture is opened and sheet material re-set (or replaced, in case of using sheaths).

Figure 2A:
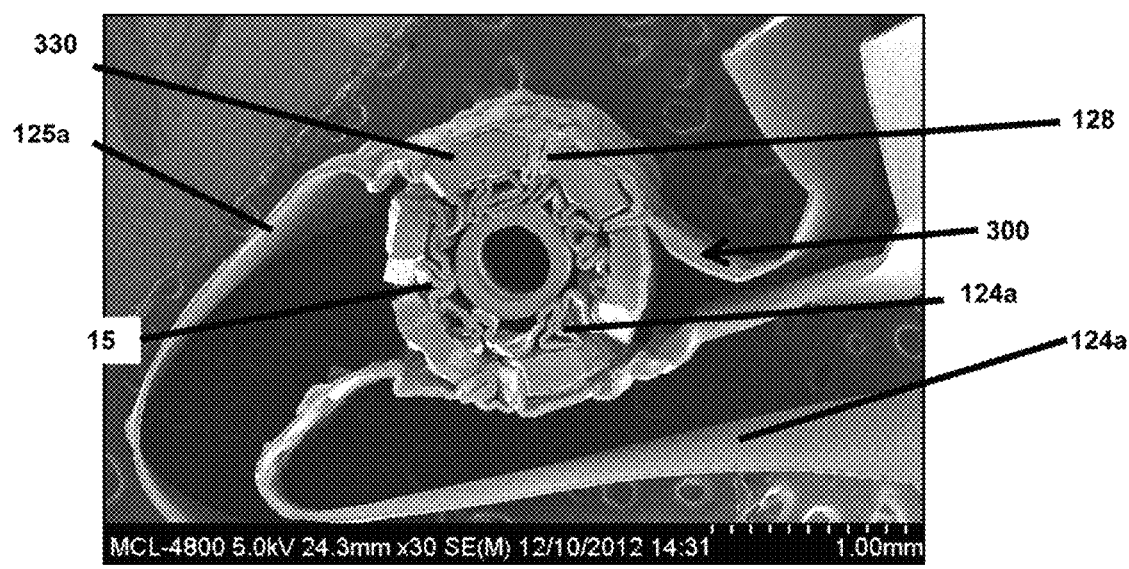
FIGS. 2A-2B are scanning electron microscope (SEM) images of a cross-section of a scaffold partially crimped to a catheter balloon within a crimp head. Polymer sheets of the crimping mechanism are wrapped around the scaffold with portions lodged between scaffold struts.
Figure 2B:
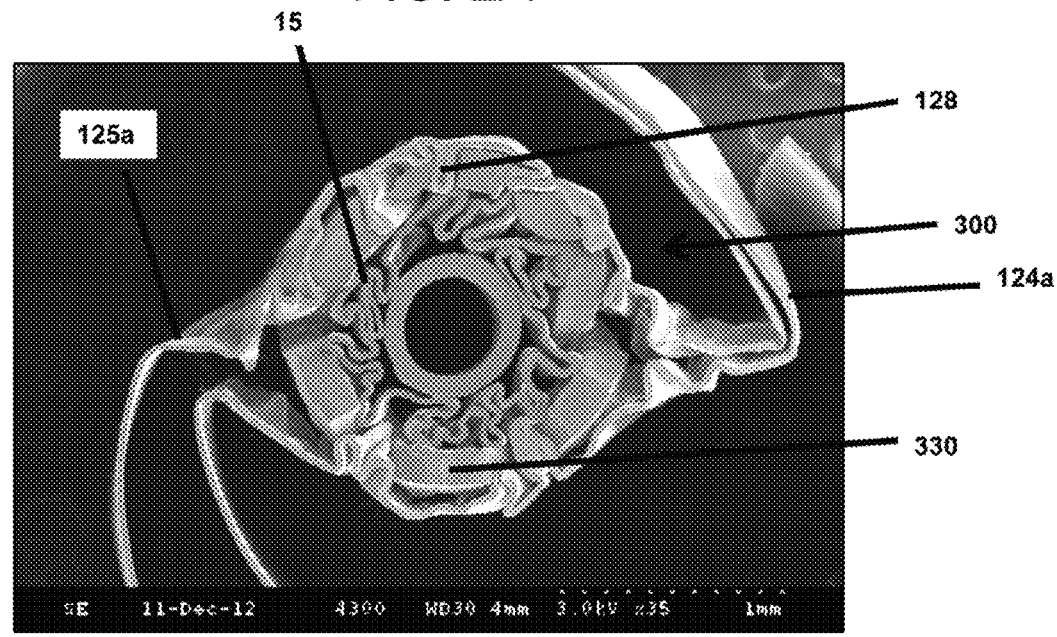

FIGS. 2A-2B illustrates what happens when polymer sheet material becomes slack when the diameter and blades are not removed to re-set the sheets, or the sheets are not otherwise kept relatively taut near the scaffold surface. Shown is the inside of the crimp head of a film-headed crimper. Although the film-headed crimper includes the tensioning mechanism mentioned above, sheet material nonetheless becomes lodged between struts of the scaffold because the blades' proximity to the scaffold surface limits the effectiveness of the tensioning mechanism. Basically, during a crimp stage or diameter reduction between stages the blades are pressing down on the scaffold surface, or the blades are very near the scaffold surface, thereby restraining movement of the polymer material disposed between the blades and scaffold surface when tension is applied to the sheet material portions outside of the aperture. The tension applied outside the blade is reacted by a pinching force on the polymer material resulting from polymer material being pinched between the blade and scaffold. As shown the scaffold 300 (partially crimped to balloon 15) has struts 330. Portions 128 of the sheets 124a/125b are caught between the folding struts 330. As these struts attempt to fold about crowns, thereby reducing ring sizes and diameter of the scaffold, the slack polymer material 128 is drawn or pushed into open spaces between struts by the converging blades. This can be easily seen in FIGS. 2A-2B. Particularly for thin-walled scaffold struts, excessive interaction of the pinched sheets with the folding struts tends to result in unsatisfactory crimped units.

Re-setting or removal of the excessive polymer material after diameter reductions (by withdrawing the blades or increasing the aperture size, in order to allow the outside tensioning to pull the polymer material away from the scaffold surface) was found to make a significant difference in the quality of crimp or production yield. It was found through testing and experimentation that a re-set or removal of excessive polymer sheet material (or in the alternative embodiment replacing a first sheath with a second, smaller sheath) at critical times (as explained below), following a diameter reduction, can prevent the polymer material from significantly interfering with the desired folding of ring struts about crowns in subsequent diameter reduction steps.

As discussed earlier in reference to FIG. 1B, for the film-headed crimper a first sheet 125a and a second sheet 124a are positioned relative to the wedges or blades 22 of the crimping device while the scaffold (or stent 100) is within the aperture of the crimping assembly 20. The two sheets are passed between two blades 22 on opposite sides of the stent 100 and a tension T1 and T2 applied to gather up excess sheet material as the iris of the crimping assembly is reduced in size via the converging blades 22. Although this tensioning mechanism is intended to keep the sheets relatively taut, the sheet material nonetheless builds up in an unacceptable manner, as explained above.

FIGS. 3A, 3B (Process I) and FIGS. 4A, 4B (Process II) are flow diagrams illustrating two examples of crimping processes that can achieve the foregoing objectives for scaffolds, including thin-walled scaffolds. In each of these examples the scaffold is crimped to the balloon is laser cut from a radially expanded tube. However, the crimping process is not limited to a scaffold made from a laser-cut tube. Other scaffold types, e.g. a scaffold not radially expanded, or scaffolds fabricated from a polymer sheet (as opposed to a tube) are within the scope of disclosure. Additionally, the starting outer diameter sizes for the scaffold, e.g. a coronary scaffold, can be between 3.0 mm and 4.25 mm, or between 6 mm-10 mm, outer diameter size for a peripheral scaffold.

Crimping Processes I and II may use one or two balloons. The two balloons referred to in the figures and below discussion are called "Balloon A" and "Balloon B." The Balloon A refers to the balloon of the balloon catheter of the finished product. The Balloon B refers to a temporary or sacrificial balloon, or balloon catheter that is used during the initial stages then replaced by the Balloon A at the time of a final alignment check, as explained below. Practice of the Process I or Process II using Balloon B (later replaced by Balloon A) is desirable when the starting inner diameter size of the scaffold is larger than, or the same size as the diameter of the Balloon A when Balloon A is inflated to its nominal inflation diameter, or when Balloon A is inflated beyond this size.

In a preferred embodiment of a crimping process a film-headed crimper is used to crimp the scaffold to the balloon catheter. For a film-headed crimper, polymer material in the form polymer sheets dispensed from a pair of rolls (FIGS. 1A-1B) is used to protect the scaffold from the blades of the crimper. Thus for this type of crimper "the re-set of polymer material within the aperture" steps means the process of opening the aperture to cause automatic removal and re-tensioning of the polymer sheets. It will be understood, however, that the invention is not limited to using a film-headed crimper, and may be practiced by alternative arrangements for placing and removing or re-setting of polymer material within the crimp aperture, e.g., using multiple sheaths.

Referring to FIGS. 3A-3B, two crimper settings or setups are used. The first crimper setup is used for the crimping stages that precede a final alignment check (FIG. 3A) and the second crimper setup is used for the stages that follow the final alignment check (FIG. 3B).

Pre-Crimp Procedure:

The scaffold is placed on Balloon A (or Balloon B if two balloons will be used). The balloon is inflated to its nominal diameter or post-dilation diameter (greater than nominal diameter size) or, more generally, the balloon is fully inflated so that its size is at least equal to or exceeds the inner diameter of the scaffold in order to support the scaffold during the initial crimping steps. The scaffold is aligned with proximal and distal markers on the balloon (not necessary if Balloon B is used). The crimper head, scaffold and/or balloon may also be deionized to remove static charge buildup that can cause the scaffold to shift out of alignment with balloon markers during crimping. Static charge buildup has been found to not only cause misalignment between the scaffold and balloon, but also cause irregular crimping of the scaffold (metal stents typically do not have static charge buildup because the balloon is in sliding contact with a metal, as opposed to a polymer surface). The scaffold is then inserted into the crimper head while the balloon remains fully inflated.

Stage I:

The scaffold supported on the fully inflated balloon is within the crimp head. The temperature for crimping or crimping temperature is set during this stage, as is the starting iris or aperture size corresponding to the input outer diameter of the scaffold (e.g. 3.5 mm). In a preferred embodiment blades of an iris or sliding wedge crimping device are heated to achieve the desired crimping temperature (alternatively a heated fluid may be used). After the scaffold reaches the crimping temperature, the iris of the crimper closes to reduce the scaffold inner diameter (ID) to less than the outer diameter (OD) of the fully inflated balloon and while the balloon remains fully inflated.

Stage II:

The crimper jaws are held at a fixed diameter for a dwell period and while the balloon is fully inflated. At the conclusion of this dwell period the scaffold and fully inflated balloon are removed from the crimping device.

Verify Alignment/Replace Balloon:

Removal after Stage II may be skipped if there is no need to check or verify final alignment with balloon markers, or if Balloon A is used for Stages I and II. In the illustrated embodiment the scaffold supported on the fully inflated balloon is removed from the crimping device to verify that the balloon is located between the balloon markers (when Balloon A used for Stages I and II), or Balloon B is replaced with Balloon A and the scaffold aligned with the balloon markers.

Referring now to FIG. 3B, Process I continues. The crimping steps illustrated in FIG. 3B use a crimping setup different from the crimping setup in FIG. 3A.

Stage III:

After the scaffold and fully inflated Balloon A are returned to the crimper, the iris diameter is set at a slightly higher diameter than the scaffold diameter at the conclusion of Stage II (to account for recoil). The iris or aperture size is held constant for a time period sufficient to bring scaffold temperature back to crimping temperature.

After the crimping temperature is reached, the scaffold diameter is reduced down while the balloon is pressurized. The balloon is preferably fully inflated for the diameter reduction following Stage III.

Stage IV:

The crimp aperture is held constant for a dwell period after scaffold diameter is reduced from the Stage III diameter. Following Stage III the polymer sheets of the film headed crimper are re-set to remove excess sheet material from within the aperture when the scaffold diameter was reduced from the Stage II diameter to the Stage IV diameter, or when the diameter was reduced from the initial diameter to the Stage IV diameter.

Balloon pressurization in the crimping process helps ensure, or improves scaffold retention on the balloon. The pressure is relieved after 50%-75% of the final crimp dwell period is complete. Typically 75-250 psi is applied. The pressure is selected to achieve the lowest possible crossing profile and ensure sufficient retention.

Stages V-VIII:

These stages follow a similar process as in Stages III-IV: perform a dwell at each of the stages with a diameter reduction between the stages. After the dwell period, the aperture is fully opened and the excess polymer sheet material removed from the aperture. In total there are three illustrated re-sets of the polymer material in the example of FIGS. 3A-3B. The re-sets all occur following the final alignment check.

Optional Stages/Final Crimp:

Following the re-set (immediately after Stage VIII) there may be a number of additional, optional stages. At the conclusion of these stages there is a final pressurization of the balloon at the final crimp diameter. The pressurization may be a leak check. After this final step the scaffold is fully crimped to the balloon catheter, removed from the crimp head and placed within a constraining sheath.

FIGS. 4A-4B describe an alternative crimping process. The description accompanying FIGS. 3A-3B applies in the same manner to FIGS. 4A-4B, except as follows. A different crimper device or setup is used for Process I after the final alignment check. Step III through Step VIII in Process I is performed on a different crimper device or setup. A re-set of the polymer material therefore may be automatically done at the time of the final alignment check in Process I (after Stage II and before Stage III). This is why a re-setting of polymer material within aperture is not shown in FIG. 3A. In Process II a single crimping device or setup (recipe) is used for the crimp. At the conclusion of Stage II of Process II (FIG. 4A) the polymer material is re-set. The re-set may be done before or after the alignment check and/or changing of balloons (when Balloon B is used for Stage I and Stage II), assuming the final alignment check is even done (this step is optional in some embodiments). Process I and Process II have a total of four illustrated steps where polymer material within the aperture is re-set. For Process I there may be an additional re-set step that is essentially done when the second crimping device/setup is used following the alignment check (thus, bring total of 4 re-sets for Process I). The number of re-sets for a particular scaffold size, balloon size and associated D-min (defined below) is chosen in an optimal fashion, based on examination of the scaffolds crimped to balloons. The criterion used to judge the effectiveness of a selected number of re-sets was the foregoing three listed objectives for crimping (structural integrity, scaffold retention and uniform expansion). It will be appreciated that polymer material interference with strut folding, especially the kind illustrated in FIGS. 2A-2B, can negatively affect any, or all three of the crimping objectives. Balanced against the desire to re-set polymer material is the time needed to re-set and output yield benefits. Decreasing the amount of diameter reduction between each stage, followed by a re-setting of material each time may, or may not necessarily make a big difference in crimp quality, but it would likely make the crimp process prohibitively complicated and time-consuming (especially for production-level crimping).

Critical Crimping Periods

According to one embodiment, a re-set of the polymer material should be employed whenever the space between struts is large enough to receive sheet material (near final crimp diameters spaces between struts may be too small for sheet material) and there has been a sufficient percentage of diameter reduction to cause material between the blades and scaffold surface to build up. This period of diameter reduction and resulting crimp size will be referred to as a critical crimping period.

The number of re-sets cannot be excessive because then the crimp process becomes too time consuming. Thus, it is not believed feasible or cost-effective to implement a re-set whenever the scaffold is reduced in diameter. A balance is needed. Re-set points within critical crimping periods should be chosen so that production yield is favorable but crimp time does not become overly burdensome.

Based on extensive testing of different scaffold types, critical crimp periods may employ one or more re-set of polymer material within the aperture ("re-set") according to one or more of the following rules:

A first re-set employed after about 30-35% reduction from the initial diameter, depending on scaffold initial diameter size (smaller starting size means re-set more likely needed in this range). This re-set may correspond to the time when the scaffold is removed from the crimper and alignment checked (or switching to Balloon A);

Two or more re-sets may be chosen based on the total travel from initial diameter to final crimp diameter; e.g., for diameter reductions of 2:1 (initial diameter to final diameter) use 2 re-sets, for 3:1 or above 3:1 use 3 or more re-sets;

For scaffold designs where struts closer together use more resets;

Employ a re-set whenever there has been a diameter reduction of about 30-35% between stages, but not to exceed in total 2, 3 or 4 re-sets for the entire crimping process; and/or Limit to maximum of 5 or between 2 and 5 re-sets. However, more re-sets are certainly possible and may be needed to achieve a desired outcome.

Scaffold and Catheter

Figure 6:
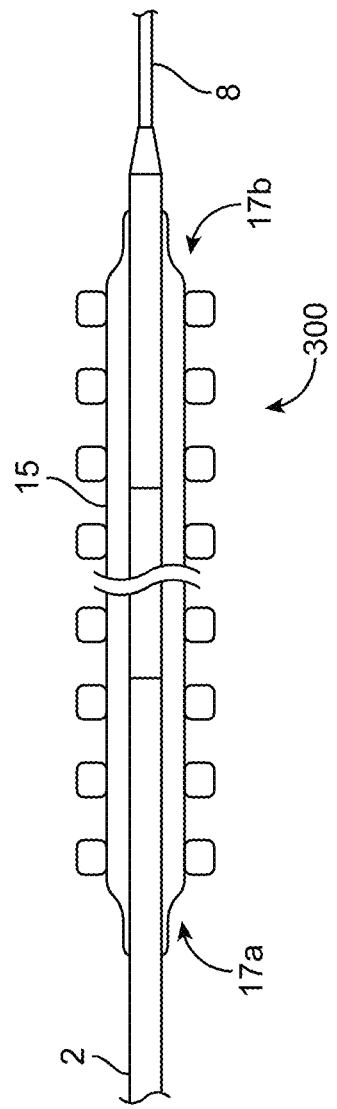
FIG. 6 shows the scaffold of FIG. 5 crimped to a balloon of a balloon catheter.

FIG. 6 illustrates a side-view of a scaffold 300 crimped to a balloon catheter, which has a shaft 2, balloon 15 with distal and proximal ends 17a, 17b (where balloon markers are found). The catheter is supported on a mandrel 8.

FIG. 5 shows a partial, planer view of end portions of the scaffold 300 from FIG. 6 in an expanded or before-crimping state. This figure illustrates an example of a network of struts and links for the scaffold 300. The left or distal end portion 302 (i.e. the left side of FIG. 5) includes sinusoidal rings 312a, 312b, and 312c where ring 312a is the outermost ring. Ring 312a and ring 312b are adjoined by two links 334 and a marker link 20. Ring 312c and ring 312d are adjoined by three links 334 that extend parallel to axis A-A. The links 334 extend parallel to axis A-A and have a constant cross-sectional moment of inertia across its length, meaning link 334 has a constant width and thickness and the location of the centroid or geometric center (or longitudinal axis) of the link is everywhere parallel with axis A-A. The right or proximal end portion 304 (i.e. the right side of FIG. 3) includes sinusoidal rings 312d, 312e, and 312f where ring 312f is the outermost ring. Ring 312d and ring 312e are adjoined by three links 334. Ring 312e and ring 312f are adjoined by two links 334 and the marker link 20. Thus, scaffold 300 has a marker link 20 extending between and adjoining the outermost link with the adjacent, inner ring. The scaffold 300 may have 15, 18 or 20 rings 312 interconnected to each other by links 334.

A ring 312, e.g., ring 312b, is sinusoidal meaning the curvature of the ring along axis B-B is best described by a sine wave where the wavelength of the sine wave is equal to the distance between adjacent crests 311a of the ring. The ring has a constant width at both crowns 307, 309 and 310 and struts 330, which connect a crown to an adjacent crown.

There are three crown types present in each inner ring 312b through 312e: U-crown, Y-crown and W-crown. Outermost rings have only the Y-crown or W-crown type, and the U-crown type. A crest or peak 311a (or trough or valley 311b) may correspond to a U-crown, Y-crown or W-crown. For the outermost ring 312a there is only a U-crown and W-crown type. For the outermost ring 312f there is only a U-crown and Y-crown type. A marker link 20 adjoins rings by forming a W-crown with the first ring (e.g., ring 312e) and a Y-crown with the second ring (e.g. ring 312f).

A link 334 connects to ring 312f at a Y-crown 310. A "Y-crown" refers to a crown where the angle extending between a strut 330 of a ring 312 and the link 334 is an obtuse angle (greater than 90 degrees). A link 334 connects to ring 312a at a W-crown 309. A "W-crown" refers to a crown where the angle extending between the strut 330 and the link 334 is an acute angle (less than 90 degrees). A U-crown 307 is a crown that does not have a link connected to it. Marker link 20 connects to a ring at a W-crown 314 and a Y-crown 316.

For the scaffold 300 there are 6 crests or peaks 311a and 6 troughs or valleys 311b for each ring 312. A crest 311a is always followed by a valley 311b. Ring 312b has 12 crowns: 3 are W-crowns 309, 3 are Y-crowns 310 and 6 are U-crowns 307.

A crimped diameter enforced on scaffold 300 (using, e.g., Process I or Process II) may be expressed in terms of a theoretical minimum crimped diameter where struts that converge at the same crown are in contact with each other when the scaffold is fully crimped, i.e., when the scaffold is removed from the crimping device, or when placed within a restraining sheath soon after crimping. The equation for the theoretical minimum crimped diameter (D-min) under these conditions is shown below $$D\text{-min} = (1/\pi) \times [(n \times \text{strut\_width}) + (m \times \text{link\_width})] + 2*t$$

Where

"n" is the number of struts in a ring (12 struts for scaffold 300),

"strut_width" is the width of a strut (170 microns for scaffold 300),

"m" is the number of links adjoining adjacent rings (3 for scaffold 300),

"link_width" is the width of a link (127 microns for scaffold 300), and

"t" is the wall thickness (93 microns for scaffold 300).

Hence, for scaffold 300 D-min=$(1/\pi) \times [(12 \times 170)+(3 \times 127)]+2 \times (93)=957$ microns. As can be appreciated D-min according some embodiments for crimping is not a function of a non-zero inner crown radius (as will be appreciated if the crimping did not exceed the inner crown radius then this additional sum of distances, i.e., twice the inner crown radius for each crown of a ring, would be added to D-min). Thus D-min defined above is less than a D-min where crimping does not bring struts into contact.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method, comprising:
    using a scaffold made from a tube comprising a polymer, the polymer having a glass transition temperature, the scaffold having an outer diameter and the outer diameter having a before crimping size;
    using a balloon having a nominal diameter;
    using a crimping device having a plurality of blades configured to form an aperture, wherein the blades are rotated relative to each other to increase or decrease the size of the aperture during crimping;
    using a polymer material disposed within the aperture; and
    crimping the scaffold to the balloon, the crimping comprising:

placing the scaffold and the balloon within the aperture, wherein the polymer material is between a surface of the scaffold and a surface of the blades, reducing the diameter of the scaffold from the before crimping size to a first size, after the scaffold has about the first size, resetting the polymer material within the aperture, reducing the diameter of the scaffold from the first size to a second size, after the scaffold has about the second size, resetting the polymer material within the aperture, and reducing the diameter of the scaffold from the second size to a third size or a final crimp size.

2. The method of claim 1, wherein the crimping device is a film-headed crimper.

3. The method of claim 1, wherein the polymer material are polymer sheets.

4. The method of claim 1, wherein the polymer material comprises a plurality of sheaths.

5. The method of claim 1, wherein the scaffold has a crimping temperature during crimping.

6. The method of claim 1, wherein the before crimping size is greater than the nominal diameter of the balloon.

7. The method of claim 1, wherein the balloon is pressurized during each of the reducing the diameter steps.

8. The method of claim 1, wherein the crimping step further includes the step of removing the scaffold and balloon from the crimping device after the scaffold diameter is reduced to the first size, then returning the scaffold to the crimping device.

9. The method of claim 8, wherein the resetting of the polymer material after the scaffold has about the first size occurs when the scaffold and balloon are removed from the crimping device.

10. The method of claim 8, wherein the balloon is a first balloon, further including the step of replacing the first balloon with a second balloon of a balloon catheter when the scaffold is removed from the crimping device, and the scaffold is crimped to the second balloon.

11. The method of claim 1, wherein the polymer material within the aperture is re-set more than 2 times during the crimping.

12. The method of claim 1, wherein before and after reducing the scaffold diameter from the first size to the second size the aperture is held constant while the balloon has the nominal diameter.

13. A method of crimping a stent, comprising:
performing a crimping procedure, the crimping procedure comprising
(i) position the stent over a balloon and within an aperture of a crimping device;
(ii) providing a sheet within the aperture to protect the stent; and
(iii) reducing a diameter of the stent by reducing a diameter of the aperture of the crimping device;
wherein the reducing the diameter of the stent is performed in multiple stages of diameter reduction until a final crimped diameter is reached, wherein the sheet is reset at least 2 times but no more than 5 times until the stent is crimped to the final crimped diameter, the reset occurring only when the diameter of the stent is reduced by about 30-35% between any of the stages, and the reset occurring only when the aperture of the crimping device is in an open position so as to not interfere with the resetting of the sheet.

14. The method of claim 13, additionally comprising performing a pre-crimping procedure, the pre-crimping procedure comprising
(a) placing the stent over the balloon or a pre-crimping balloon;
(b) inflating the balloon or the pre-crimping balloon by application of a pressure; and
(c) reducing the diameter of the stent to a diameter selected for the start of the crimping procedure, wherein if a pre-crimping balloon is used, the stent is then transferred to the balloon from the pre-crimping balloon before the start of the crimping procedure.

15. The method of claim 13, additionally comprising performing a pre-crimping procedure, the pre-crimping procedure comprising
(a) placing the stent over the balloon or a pre-crimping balloon;
(b) placing the stent within the aperture of the crimping device;
(c) setting the diameter of the aperture of the crimping device to a selected size;
(d) optionally heating the stent while the diameter of the aperture is maintained the selected size;
(e) inflating the balloon or the pre-crimping balloon by application of a pressure; and
(f) reducing the diameter of the stent to a diameter selected for the start of the crimping procedure, wherein if a pre-crimping balloon is used, the stent is then transferred to the balloon from the pre-crimping balloon before the start of the crimping procedure.

16. The method of claim 13, wherein each stage of the multiple stages of diameter reduction comprises:
(a) having the aperture of the crimping device at a selected size;
(b) optionally heating the stent while the aperture is maintained at the selected size;
(c) inflating the balloon to a selected size by application of a pressure;
(d) reducing the diameter of the stent to a selected size by reducing the size of the aperture; and
(e) maintaining the aperture of the crimping device for a dwell period of time when the stent reaches the selected size.

17. A method, comprising:
using a scaffold made from a tube comprising a polymer, the polymer having a glass transition temperature, the scaffold having an outer diameter and the outer diameter having a before crimping size;
using a balloon having a nominal diameter;
using a crimping device having a plurality of blades configured to form an aperture;
using a polymer material disposable within the aperture; and
crimping the scaffold to the balloon, the crimping comprising:
placing the scaffold and balloon within the aperture so that the polymer material is between a scaffold surface and a surface of the blades,
reducing the diameter of the scaffold from the before crimping size to a final crimped size, wherein the polymer material within the aperture is reset, when the aperture is in an open state, between 2 and 5 times while the scaffold diameter is reduced from the before crimping size to the final crimped size.

18. The method of claim 17, wherein the polymer material comprises sheaths having different sizes.

19. The method of claim 17, wherein the polymer material are sheets operated by a film-headed crimper.

20. A method, comprising:
using a scaffold made from a tube comprising a polymer, the polymer having a glass transition temperature, the scaffold having an outer diameter and the outer diameter having a before crimping size;
using a balloon having a nominal diameter;
using a crimping device having a plurality of blades configured to form an aperture, wherein the blades are rotated relative to each other to increase or decrease a size of the aperture during crimping;
using a polymer material disposable within the aperture; and
crimping the scaffold to the balloon, the crimping comprising:
placing the scaffold and balloon within the aperture,
reducing the diameter of the scaffold from the before crimping size to a first size that is between 30% to 35% less than the before crimping size,
after reducing the diameter to the first size, increasing the aperture size to remove a pressure of the blades from a surface of the scaffold, followed by removing excess polymer material from the aperture,
after removing the polymer material, decreasing the aperture size,
reducing the scaffold diameter from the first size to a second size,
after reducing the diameter to the second size, increasing the aperture size to remove a pressure of the blades from the surface of the scaffold, followed by removing excess polymer material from the aperture,
after removing the polymer material, decreasing the aperture size, and
reducing the scaffold diameter from the second size to a third size or a final crimp size.

* * * * *